United States Patent [19]

Hommeltoft et al.

[11] Patent Number: 6,123,836

[45] Date of Patent: *Sep. 26, 2000

[54] PROCESS FOR THE REMOVAL OF ACID COMPOUNDS FROM A HYDROCARBON STREAM

[75] Inventors: Sven Ivar Hommeltoft, Hillerød; Karsten Laurents, Lyngby, both of Denmark

[73] Assignee: Haldor Topsoe A/S, Lyngby, Denmark

[*] Notice: This patent issued on a continued prosecution application filed under 37 CFR 1.53(d), and is subject to the twenty year patent term provisions of 35 U.S.C. 154(a)(2).

[21] Appl. No.: 09/109,523

[22] Filed: Jul. 2, 1998

[30] Foreign Application Priority Data

Jul. 4, 1997 [DK] Denmark .................................. 0804/97

[51] Int. Cl.[7] .............................. C10G 25/00; C07C 2/56; C07C 2/58; C07C 2/66

[52] U.S. Cl. ........................... 208/299; 208/307; 585/447; 585/458; 585/730; 585/720

[58] Field of Search ..................................... 208/263, 299, 208/307; 585/447, 458, 730, 720

[56] References Cited

U.S. PATENT DOCUMENTS 2,981,771  4/1961  Brant et al. ......................... 260/683.62
5,396,018  3/1995  Hommeltoft .............................. 585/724

*Primary Examiner*—Marian C. Knode
*Assistant Examiner*—Tam M Nguyen
*Attorney, Agent, or Firm*—Ostrolenk, Faber, Gerb & Soffen, LLP

[57] ABSTRACT

Process for the removal of acid compounds contained in a hydrocarbon process stream by passing the process stream through a fixed bed of an adsorption material at conditions where the acid compounds adsorb on the material and withdrawing a purified hydrocarbon process stream, wherein water has been adsorbed on the material prior to contact with the hydrocarbon process stream.

10 Claims, No Drawings

PROCESS FOR THE REMOVAL OF ACID COMPOUNDS FROM A HYDROCARBON STREAM

The present invention relates to a process for the removal of acid compounds from a hydrocarbon stream. The invention is in particular useful in the removal and recovery of dissolved acids and acid derivatives from an effluent stream of hydrocarbon containing acid compounds.

Isobutane alkylation is an example of a process that can be catalysed by a liquid Brønsted acid such as sulphuric acid or fluorinated acids.

The product stream from an alkylation reactor can contain dissolved acids or derivatives thereof which have to be removed from the product.

In U.S. Pat. No. 5,396,018 a method is described for the recovery of an acid catalyst from an acid catalyzed conversion process by passing a product stream of converted hydrocarbons leaving the hydrocarbon conversion process and containing the acid catalyst through a fixed bed of a solid absorbent material; and desorbing the absorbed acid catalyst into a process stream of hydrocarbons being passed through the adsorbent bed.

Though this process removes all acid from the product stream in a sample passage through the adsorbent and most of the acid after desorption, small amounts of the acid remain on the absorbent and are not recycled after a number of adsorption and desorption cycles using a hydrocarbon stream for the desorption.

Another disadvantage of this process is that the absorbent has a limited capacity and has to be regenerated frequently.

A further disadvantage is that an absorbent, which is efficient for the removal of acid from a hydrocarbon stream is less efficient for the removal of esters of the acid that may be present in the effluent from an alkylation process.

U.S. Pat. No. 5,603,812 discloses a method for recovering fluorinated sulphonic acids from aqueous solutions and U.S. Pat. No. 5,220,095 discloses extraction of acid from a hydrocarbon stream by water.

The general object of this invention is to provide an efficient process for the removal of acid compounds, e.g. sulphonic acids and esters of these acids from acid catalyst process effluents including alkylation processes.

Accordingly, this invention provides a process for the removal of acid compounds contained in a hydrocarbon process stream by passing the process stream through a fixed bed of an adsorption material and thereby adsorbing the acid compounds and withdrawing a purified hydrocarbon process stream, wherein water has been adsorbed on the adsorbent material prior to contact with the hydrocarbon process stream.

The inventive process is particularly useful for the removal of fluorinated alkane sulphonic acids and their ester derivatives from product streams from an alkylation process such as described in U.S. Pat. No. 5,220,095 and U.S. Pat. No. 5,245,100.

The inventive process provides the quantitative recovery of the acid compounds in an aqueous solution.

When operating the invention, a product stream from a hydrocarbon conversion process is brought into contact with a moisturised adsorbent, which adsorbs the acid and esters contained in the product stream. In a subsequent step the acid may be recovered from the adsorbent by extraction with water. In a subsequent step, the absorbent is dried and wetted before being used in a further adsorption step.

In a preferred embodiment, a fixed bed of solid adsorbent material to which water has been added is used. The amount of water added should preferably be sufficient to wet the surface of the pores in the adsorbent material, but not be so much that the pores of the solid absorbent are saturated.

Silica gel is a suitable adsorbent material and a preferred amount of water is in the range 0.1–50% (w/w) depending on the surface area and pore volume of the silica gel. Other convenient adsorbent materials include alumina.

Water can either be evenly distributed throughout the bed or can be concentrated in the upstream end of the bed. In the latter case the lower part of the adsorbent bed may then be utilized in removing water that may be dissolved in the hydrocarbon stream after passage of the wet section of the bed.

Water for wetting the adsorbent material may be added from the end of the bed either dissolved in the hydrocarbon stream or sprayed directly onto the bed. Alternatively, the adsorbent may be wetted thoroughly and excessive amounts of water subsequently removed by partial drying.

The adsorbed acid is subsequently recovered by washing with water. Thereby, the adsorbed acid compounds can be completely extracted as an aqueous solution. After drying of the adsorbent and addition of the required amount of water, the adsorbent is completely regenerated.

EXAMPLE 1

Silica gel (Merck 100, 0.2–0.5 mm) was dried at 450° C. and subsequently wetted with 10% (w/w) water. A 3 m long, ¼" diameter tube was packed with wetted silica gel (50 ml) and used as adsorber. The tube was submerged in a temperature controlled bath at 30° C. and floated with liquid isobutane at sufficient pressure to keep the isobutane in liquid form. An isobutane stream containing 200–1000 ppm trifluoromethanesulphonic acid was passed through the adsorber at a rate of 5–10 g/min. giving a residence time of approximately 5 minutes. The effluent from the tube was analysed for its content of trifluoromethanesulphonic acid by extraction with water and measurement of the triflate content by ion chromatography.

More than 4.2 kg isobutane containing 200–1000 ppm trifluoromethanesulphonic acid were passed through the adsorber and samples of the effluent were taken at various feed flows and acid concentrations in the inlet. All effluent samples contained less than 1 ppm trifluoromethanesulphonic acid regardless of the flow and feed concentration.

EXAMPLE 2

Silica gel (Merck 100, 0.2–0.5 mm) was dried at 450° C. and subsequently wetted with 10% (w/w) water. A 3 m long, ¼" diameter tube was packed with the wetted silica gel and used as adsorber. The tube was submerged in a temperature controlled bath at 30° C. and floated with liquid isobutane at sufficient pressure to keep the isobutane in its liquid form. A feed consisting of an isobutane stream containing 0.5% (w/w) propene and 100–2000 ppm isopropyl triflate were passed through the absorber at a rate of 5–10 g/min. Samples of the effluent from the tube were analyzed for its content of trifluoromethanesulphonic acid and esters. Each sample was treated with water at room temperature for a sufficient time to allow all isopropyl triflate. to be hydrolysed to free acid 10–20 hours. The trifluoromethanesulphonic acid was extracted with water and the triflate content in the aqueous extract was measured by ion chromatography.

After passage of 3942 g feed mixture, the effluent hydrocarbon samples still contained less than one ppm triflate. In subsequent samples the triflate content gradually increased to more than 100 ppm indicating an ester breakthrough in the adsorber.

The adsorber was subsequently washed with water to recover amounts of adsorbed trifluoromethanesulphonic acid ester. An aqueous solution containing 3.8 g trifluoromethanesulphonic acid was thereby recovered.

EXAMPLE 3 (COMPARISON EXAMPLE)

In this experiment the conditions were the same as in Example 3 with the exception that the silica gel used as adsorber was dry.

After passage of 530 g of feed mixture the triflate content in the effluent rapidly increased from below 1 ppm. In subsequent samples the triflate content in the effluent was above 100 ppm.

The adsorber was subsequently washed with water to determine the total amount of trifluoromethanesulphonic acid adsorbed. 0.3 g was found.

EXAMPLE 4 (COMPARISON EXAMPLE)

40 ml petroleum ether containing approximately 4000 ppm trifluoromethanesulphonic acid in form of isopropyl ester were stirred with 10 ml of water at room temperature. After 45 min. the ester content in the hydrocarbon phase was determined. About 50% of the initial ester were found in the hydrocarbon phase.

What is claimed is:

1. Process for the removal of acid compounds contained in a fluorinated sulphonic acid catalyzed hydrocarbon alkylation process stream, wherein the acid compounds comprise perfluorinated sulphonic acids or esters thereof, the process comprising:
    passing the process stream through a fixed bed of an adsorption material at conditions where the acid compounds adsorb on the adsorption material; and
    withdrawing a purified hydrocarbon process stream,
    wherein about 10%–50% by weight of water has been adsorbed on the adsorption material prior to contact with the hydrocarbon process stream.

2. The process of claim 1, wherein the hydrocarbon process stream is an effluent stream from an acid catalyzed alkylation process of a hydrocarbon substrate.

3. The process of claim 1, wherein the acid compound is trifluoromethanesulphonic acid and/or a triflate ester.

4. The process of claim 1, wherein the adsorbent material comprises silica and/or alumina.

5. Process according to anyone of the preceding claims comprising the further steps of recovering adsorbed acid compounds by extraction with water.

6. Process for the removal of acid compounds contained in a fluorinated sulphonic acid catalyzed hydrocarbon alkylation process stream by passing the stream through a fixed bed of an adsorption material, the acid compounds comprising perfluorinated sulphonic acids or esters thereof, the process comprising:
    adding about 10%–50% by weight water to the adsorption material prior to contact of the adsorption material with the hydrocarbon process stream;
    passing the process stream through the fixed bed of adsorption material at conditions where the acid compounds adsorb on the adsorption material; and
    withdrawing a purified hydrocarbon process stream.

7. The process of claim 6, wherein the hydrocarbon process stream is an effluent stream from an acid catalyzed alkylation process of a hydrocarbon substrate.

8. The process of claim 6, wherein the acid compound is trifluoromethanesulphonic acid or a triflate ester.

9. The process of claim 6, wherein the adsorption material comprises silica and/or alumina.

10. The process of claim 6, further comprising the step of recovering adsorbed acid compounds by extraction with water.

* * * * *